US009884204B1

(12) United States Patent
Dolleris et al.

(10) Patent No.: US 9,884,204 B1
(45) Date of Patent: Feb. 6, 2018

(54) LED MATRIX FOR SUBCUTANEOUS FAT REDUCTION WITH AN EFFICIENT COOLING SURFACE

(71) Applicant: DEL MAR TECHNOLOGIES, INC., San Marcos, CA (US)

(72) Inventors: Casper Dolleris, Vancouver (CA); Jan K. Enemaerke, San Marcos, CA (US); Edward Victor Ross, San Diego, CA (US)

( * ) Notice: Subject to any disclaimer, the term of this patent is extended or adjusted under 35 U.S.C. 154(b) by 0 days.

(21) Appl. No.: 15/385,797

(22) Filed: Dec. 20, 2016

(51) Int. Cl.
*A61N 5/06* (2006.01)
*A61N 5/00* (2006.01)

(52) U.S. Cl.
CPC ...... *A61N 5/0625* (2013.01); *A61N 2005/005* (2013.01); *A61N 2005/007* (2013.01); *A61N 2005/0626* (2013.01); *A61N 2005/0643* (2013.01); *A61N 2005/0652* (2013.01); *A61N 2005/0659* (2013.01); *A61N 2005/0667* (2013.01)

(58) Field of Classification Search
CPC .... A61N 5/0613; A61N 5/062; A61N 5/0616; A61K 38/39
USPC ........ 606/10; 607/88, 86; 257/717; 435/69.1
See application file for complete search history.

(56) References Cited

U.S. PATENT DOCUMENTS

| 5,143,063 | A | | 9/1992 | Fellner | |
|---|---|---|---|---|---|
| 5,698,866 | A | * | 12/1997 | Doiron | A61N 5/062 |
| | | | | | 257/717 |
| 7,959,656 | B2 | * | 6/2011 | Myeong | A61N 5/0613 |
| | | | | | 606/10 |
| 9,333,037 | B2 | | 5/2016 | Loeb | |
| 2003/0032143 | A1 | * | 2/2003 | Neff | A61K 38/39 |
| | | | | | 435/69.1 |
| 2005/0085875 | A1 | * | 4/2005 | Van Zuylen | A61N 5/0616 |
| | | | | | 607/88 |
| 2007/0154538 | A1 | | 7/2007 | Neuberger et al. | |
| 2007/0208395 | A1 | * | 9/2007 | Leclerc | A61N 5/0616 |
| | | | | | 607/86 |
| 2007/0213698 | A1 | | 9/2007 | Altshuler et al. | |
| 2012/0022510 | A1 | | 1/2012 | Welches et al. | |

(Continued)

FOREIGN PATENT DOCUMENTS

WO          2014149021          9/2014

*Primary Examiner* — William Thomson
*Assistant Examiner* — Victor Shapiro
(74) *Attorney, Agent, or Firm* — Arc IP Law, PC; Joseph J. Mayo

(57) ABSTRACT

A device that reduces subcutaneous adipose tissue using a matrix of LEDs to heat and destroy fat cells. The surface facing the patient's skin may be a plate of thermally conductive material such as copper or aluminum, with apertures for the LEDs. Fat reduction may be optimized using infrared LEDs with peak spectral power in the range of 920 nm to 950 nm. The device may include multiple light emitting sections connected with flexible couplings so that the device can conform to curved body shapes; treatment surfaces of individual sections may also be curved. Sections may include cooling mechanisms to cool both the LEDs and the plate facing the patient's skin, such as thermoelectric cooling elements and air or water circulation. A user interface may provide monitoring and control of treatment parameters. The device may incorporate ultraviolet LEDs to facilitate removal of an adhesive attaching the device to the patient.

19 Claims, 14 Drawing Sheets

(56) References Cited

U.S. PATENT DOCUMENTS

2012/0116484 A1  5/2012 Bornstein
2013/0338739 A1  12/2013 Bornstein
2014/0025033 A1  1/2014 Mirkov et al.

* cited by examiner

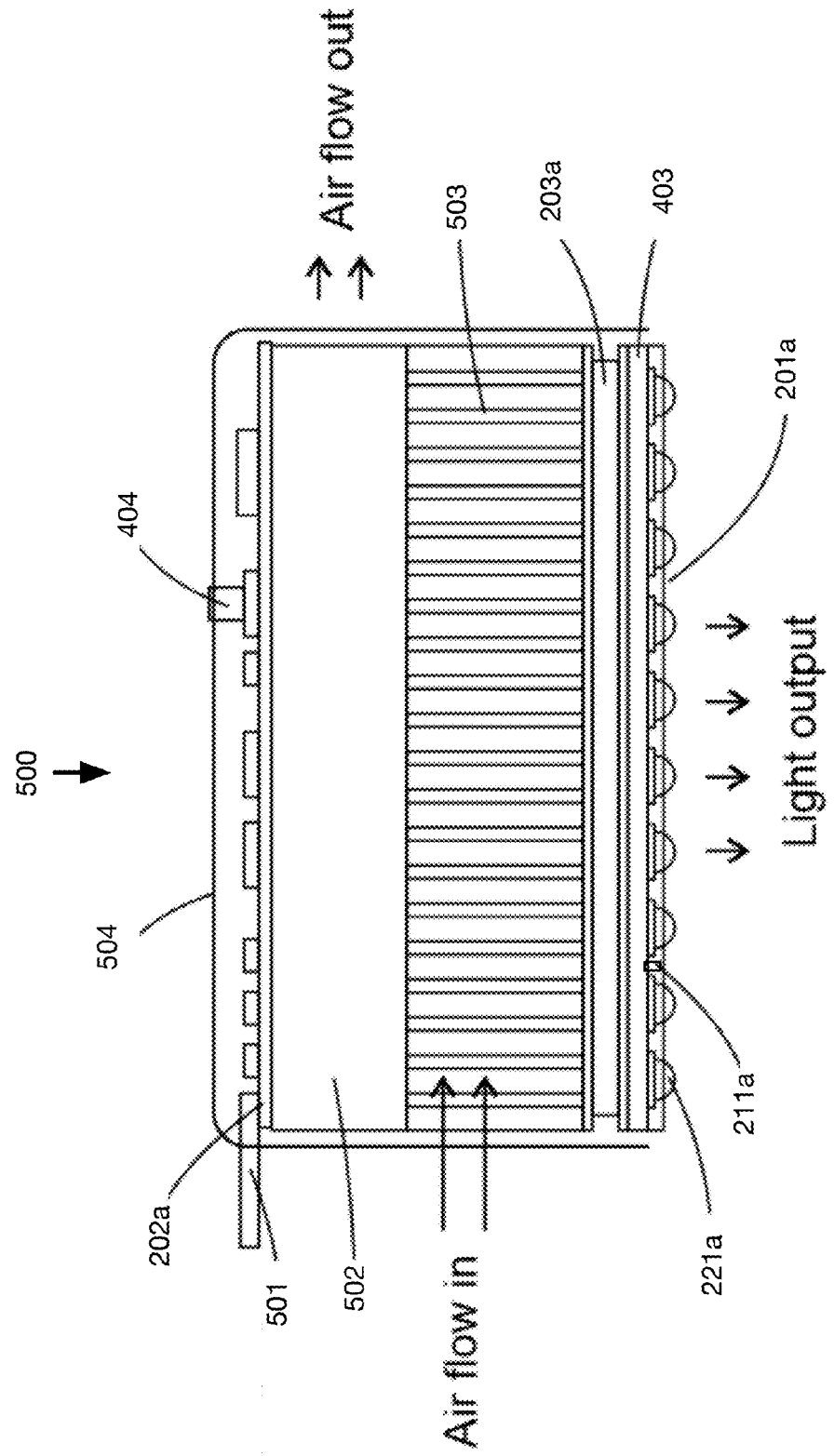

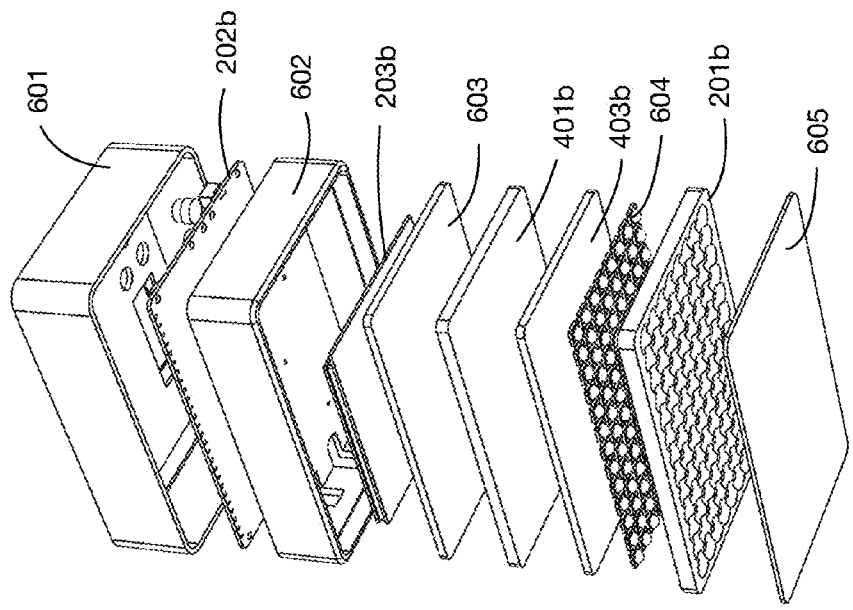
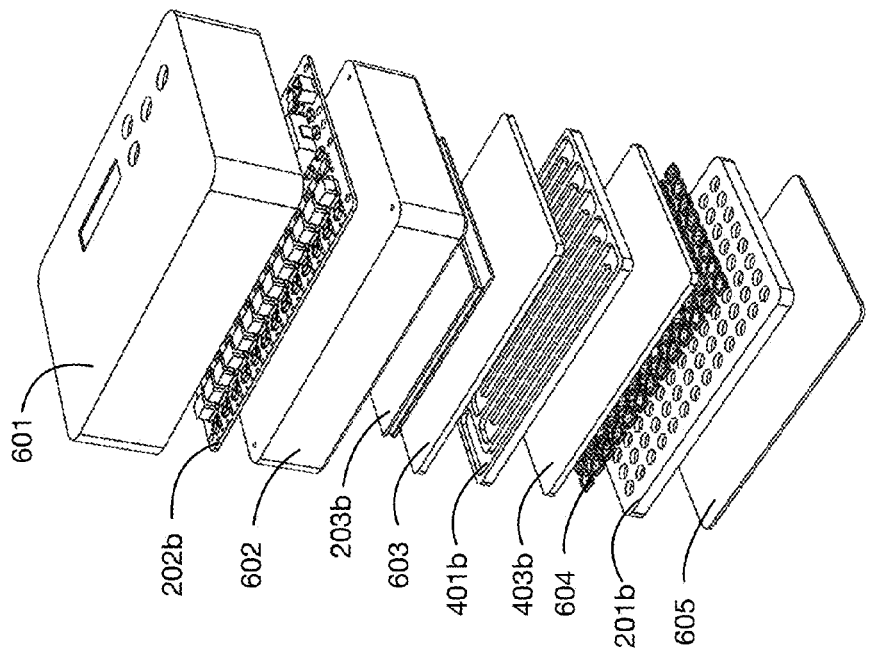

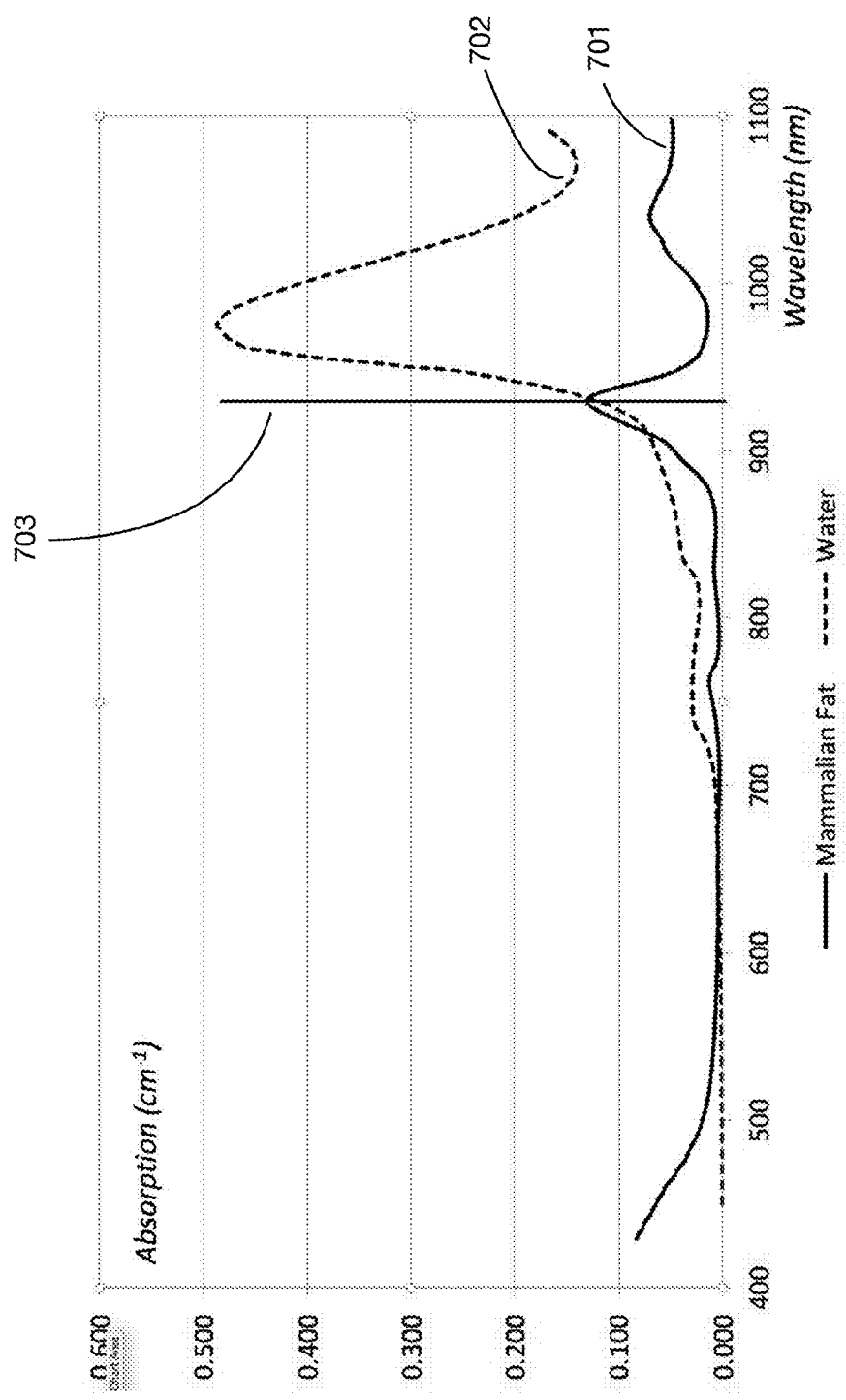

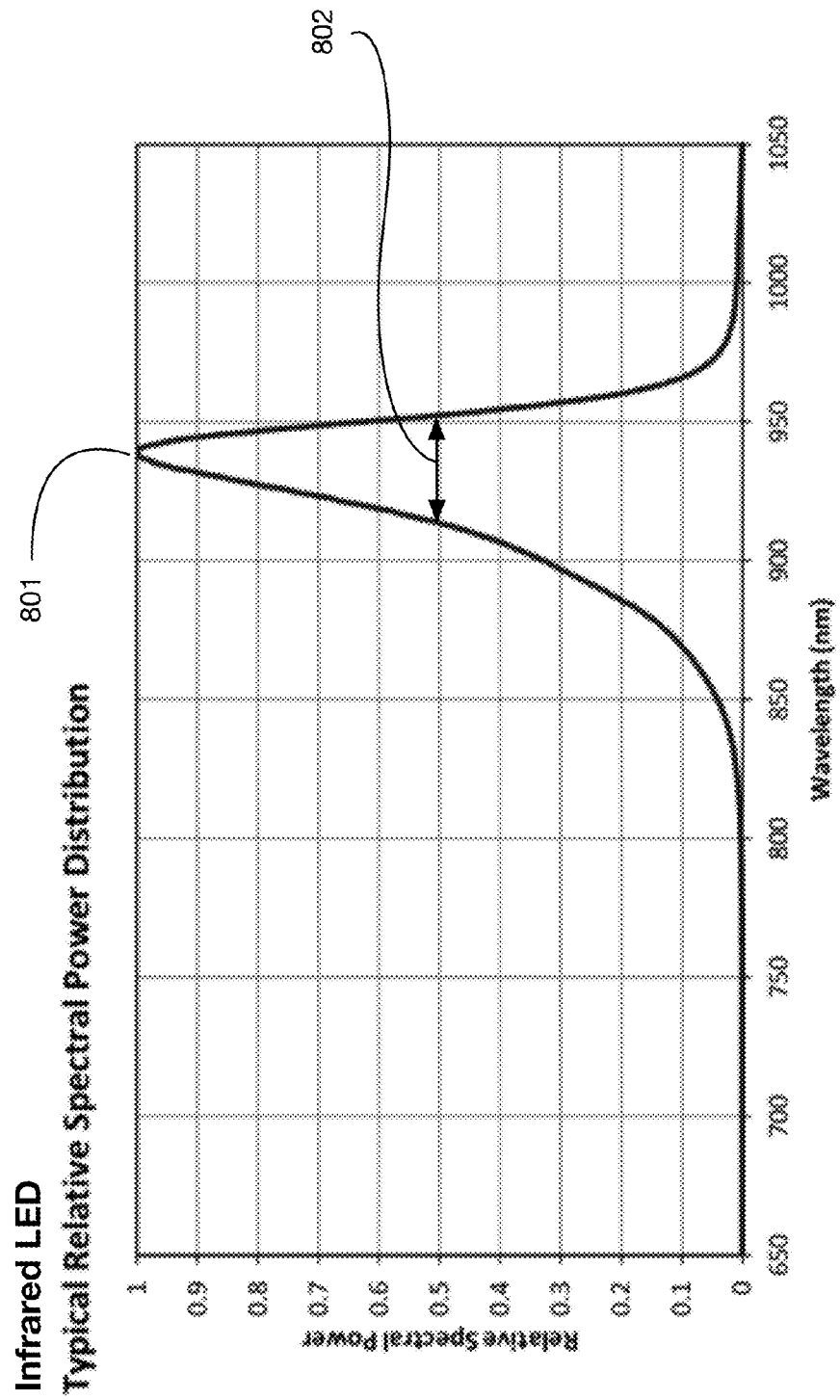

LED MATRIX FOR SUBCUTANEOUS FAT REDUCTION WITH AN EFFICIENT COOLING SURFACE

BACKGROUND OF THE INVENTION

Field of the Invention

One or more embodiments of the invention are related to the field of medical and cosmetic devices that treat tissues with electromagnetic radiation. More particularly, but not by way of limitation, one or more embodiments of the invention enable a device that treats subcutaneous fat cells with infrared radiation from an LED matrix, and that uses an efficient cooling surface to remove heat from the patient's skin during treatment.

Description of the Related Art

Fat reduction using ultrasound, RF, microwave, cold or heat technology has been demonstrated in literature and devices. More specifically, using heat to damage adipocytes has been demonstrated in sources such as United States Utility Patent 5,143,063, "Method of removing adipose tissue from the body."

Exposed to a temperature in the mid 40° C. range for a period of time, the loosely connected adipose tissue is damaged and removed over time. Since fat cells do not multiply significantly, much of this tissue is permanently removed.

One method of heating sub-surface fat cells is by light irradiation using the selective photothermolysis method—using variations in light absorption of different tissue chromophores. This selective heating is required in order to mostly heat the target tissue to the damage point, not the surrounding tissue.

In many medical devices, lasers are used as light sources for treatments based on selective photothermolysis. Lasers are effective light sources with a narrow spectral band, high brightness and in some cases high efficiency. High power lasers are for the most part expensive to manufacture due to the low quantity used in medical applications. Many medical applications require the use of laser for sufficient brightness in focusing into delivery systems, such as optical fibers and for use in devices with small high power density spots, such as fractional devices.

LEDs (light emitting diodes) are a more reliable, lower cost light source, but do not provide the extreme brightness of lasers. For this application neither high brightness, power density or fluence is required, and the exposure time is long (minutes), making this an ideal application for LED technology. LEDs have several advantages, including low cost, reliability, distributed emission of light, tolerance of higher operating temperatures, long lifetime, enhanced safety due to lower brightness, and fewer regulatory requirements.

Optimal fat reduction occurs when the wavelength of light is maintained in a range that maximizes absorption of radiation by fat cells. Because the wavelength of LED light is somewhat temperature dependent, LEDs should be cooled and temperature controlled to ensure optimal effectiveness for fat reduction. It is also desirable to cool the patient's skin so that heat can be directed at the subcutaneous fat cells without excessively heating other tissues; by cooling the skin, the device can raise the temperature of the fat cells sufficiently to remove fat without causing damage to other tissues or causing unacceptable patient discomfort.

Existing solutions for cooling the skin generally use one of two approaches. One approach is to use air cooling of the skin, for example by forcing air over the skin during treatment. This approach requires that an air gap be maintained between the LEDs and the skin, which reduces treatment effectiveness since the light source is further from the treatment area. It also may require complex and potentially expensive cooling systems such as fans. Another approach is to place a transparent window over the LEDs and to cool the window. This approach has at least two drawbacks. First, transparent materials typically do not have very high thermal conductivity, so they are not very effective at removing heat from the skin. (While sapphire, which is often used for these types of windows, has higher thermal conductivity than glass, it is still a far poorer heat conductor than a metal, for example.) Second, the windows are generally cooled only on their edges, which limits the rate at which heat can be removed in the interior of the window.

There are no known systems that provide an efficient, highly thermally conductive treatment surface for skin cooling with a matrix of LEDs that treats subcutaneous fat.

For at least the limitations described above there is a need for an LED matrix for subcutaneous fat reduction with an efficient cooling surface.

BRIEF SUMMARY OF THE INVENTION

One or more embodiments described in the specification are related to an LED matrix for subcutaneous fat reduction with an efficient cooling surface. Embodiments of the system use radiation from one or more matrices of LEDs to heat and destroy fat cells. One or more embodiments may incorporate components that cool the LEDs as well as the skin of the patient being treated, including a thermally conductive treatment surface that efficiently removes heat from the patient's skin.

One or more embodiments of the system may incorporate one or more light emission sections, also called "pods," which may form an interconnected device to treat a potentially large area of the patient's body. Each pod may have a front plate that is placed on or proximal to the patient's skin. The front plate may be made completely or partially of a thermally conductive material, such as for example, without limitation, copper, aluminum, or another metal. Each light emission section may have a matrix of LEDs that irradiate the skin of the patient, where a portion of the radiation penetrates to the subcutaneous adipose tissue, thereby heating and destroying the fat cells. The front plate may have a matrix of apertures corresponding to the LED matrix to allow light to reach the skin; the thermally conductive material in between the apertures may contact the skin to facilitate heat removal. The LEDs may be located inside or behind the apertures. Each section may have one or more temperature sensors. A section may include a cooling system that cools both the front plate facing the patient's skin and the LED matrix. A controller integrated into each section may be coupled to the components of the pod, such as the LEDs, the temperature sensors, and the cooling system. The controller may be configured to monitor and control the treatment, for example by maintaining the temperature of the skin within a target range. Temperature monitoring may be used as an alternative to, or in addition to, obtaining feedback from the patient on whether the temperature is a comfortable range for the patient.

In one or more embodiments, multiple light emissions sections ("pods") may be connected via non-rigid couplings that allow the sections to pivot with respect to one another.

This coupling allows the overall device to conform to a curved surface such as a portion of the patient's body. The couplings may for example include electrical connections as well as mechanical linkages, and may in some embodiments include paths for flow of cooling fluid.

In one or more embodiments the LEDs may have a peak spectral power in the range of 920 nanometers to 950 nanometers. This wavelength may optimize the absorption of radiation by fat cells. The controller may be configured to maintain the temperature of the LEDs in a range that keeps the peak spectral power in this target wavelength range. One or more embodiments may incorporate wavelength filters to concentrate the LED output in selected wavelength ranges, such as the range 920 nanometers to 950 nanometers. In one or more embodiments, the LED matrix of a section may be configured to irradiate the skin of a patient with at least 1 watt per centimeter squared in the treatment area.

In one or more embodiments, the apertures of the front plate may have transparent coverings. In one or more embodiments, these transparent coverings may be protrusions that extend forward (towards the patient's skin) from the front plate surface. These protrusions may for example compress the tissue under the protrusion, bringing the LEDs closer to the adipose tissue and thereby enhancement treatment effectiveness. The transparent protrusions may allow light from the LEDs to pass through to reach the patient's tissues. In one or more embodiments the transparent coverings may be lenses, or may be refract, filter, focus, diffuse, or otherwise alter the radiation emitted from the LEDs in any desired manner.

In one or more embodiments, the LEDs may be offset behind the treatment surface (in the direction away from the patient's skin); this placement may distribute radiation from the LEDs more evenly across the treatment surface. LEDs need not all be located in the same plane; in one or more embodiments, some LEDs may be located at different offsets from the treatment surface, or some LEDs may be located in protrusions extending from the front plate while other LEDs are located at or behind the surface.

In one or more embodiments, the cooling system for a light emission section may include a thermoelectric (Peltier) heating element, as well as possibly a water or air circulation system to remove heat from the hot side of the thermoelectric element. For one or more embodiments that incorporate water cooling, the cooling fluid may come from an external source, and the light emission sections may have input and output ports for the circulation of this fluid.

One or more embodiments may include a user interface, such as a user controller device or a software application with a graphical user interface. The user interface may for example include controls to increase the LED energy output, to decrease the LED energy output, or to stop output. The user interface may be used by the patient, by treatment personnel, or by a combination thereof.

In one or more embodiments, one or more of the light emission sections may have curved front plates to conform to the curved shape of the patient's body parts. Sections with curved surfaces may be combined into devices with multiple sections that can pivot with respect to one another, in order to cover a larger surface area while conforming to the shape of the patient's body.

In some applications the system may be attached to the patient's body with an adhesive. One or more embodiments may incorporate components that facilitate detachment of the adhesive. For example, one or more embodiments may include ultraviolet LEDs (in addition to the infrared LEDs used for fat treatment) that are configured to weaken the adhesive strength of the adhesive. These ultraviolet LEDs may be activated at the end of a treatment section to facilitate removal of the device from the adhesive or removal of the adhesive from the patient's skin.

BRIEF DESCRIPTION OF THE DRAWINGS

The above and other aspects, features and advantages of the invention will be more apparent from the following more particular description thereof, presented in conjunction with the following drawings wherein:

FIG. 5 shows a side view of an embodiment of the invention that is air cooled.

FIGS. 6A and 6B show exploded views of an embodiment of the invention that uses a water heat exchanger and a metal cooling transfer frame to cool the LED matrix by removing heat from a metal grid placed in front of the LEDs.

FIG. 7 illustrates the benefit of radiation near 930 nm in reducing fat, since absorption of radiation by fat cells is maximized at this wavelength.

FIG. 8 shows a typical spectral power distribution for an infrared LED that may for example be used in one or more embodiments of the invention.

DETAILED DESCRIPTION OF THE INVENTION

An LED matrix for subcutaneous fat reduction with an efficient cooling surface will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
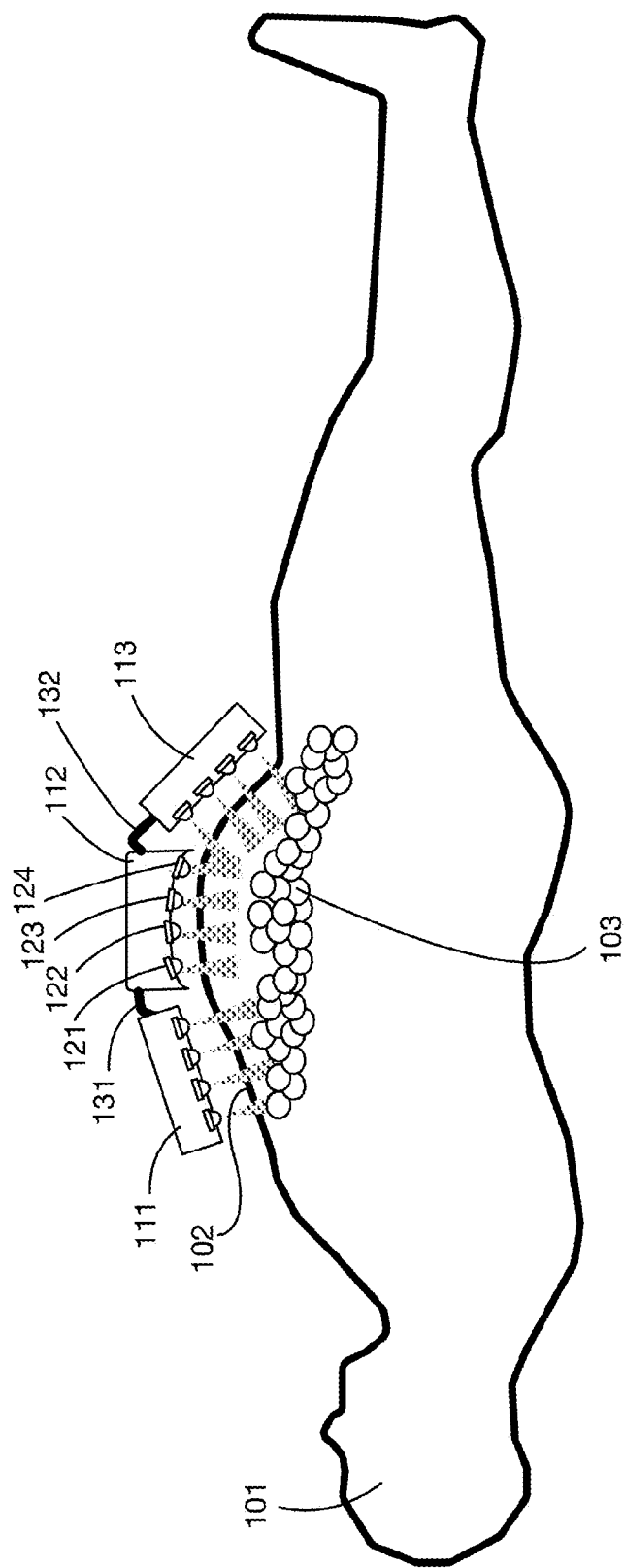
FIG. 1 illustrates an embodiment of the invention with three interconnected sections that provide infrared radiation from LEDs to remove fat cells below the skin.

FIG. 1 shows an embodiment of the invention that is treating patient 101. Infrared light from one or more LED matrices is applied to the skin 102 of patient 101; this radiation penetrates to adipose tissue 103 and destroys fat cells via heating. One or more embodiments of the system may contain one or more light emission sections, or "pods," that each may contain a matrix of LEDs as well as cooling, sensing, and control subsystems. For example, the embodiment shown in FIG. 1 has three sections 111, 112, and 113. This is illustrative; one or more embodiments may have only a single section, while other embodiments may have any number of sections. Sections may be of any size and shape. Sections may be connected or coupled via flexible or moveable structures such as couplings 131 and 132. These nonrigid couplings between sections may allow the entire device to conform better to the shape of the body of the person being treated, since sections may be able to move and pivot with respect to one another. Couplings between sections may also include electrical connections and possibly paths for flow of coolant. In one or more embodiments, individual sections may also have curved surfaces that face the patient, in order to conform to the shape of the patient's body parts. For example, section 112 in FIG. 1 has a curved surface. In one or more embodiments section surfaces may be shaped to conform to specific body parts; for example, a section may be designed for a particular body area such as a leg or an arm.

Each section may have multiple LEDs that direct radiant energy towards the skin of the patient. These LEDs may be arranged in any desired pattern. For example, section 112 has LEDs 121, 122, 123, and 124. Sections may have any number of LEDs. Different sections of a device may have different numbers of LEDs in one or more embodiments.

The section or sections of an embodiment of the invention may be configured to be placed directly against the skin of patient 101, or to be placed proximal to the skin. In one or more embodiments an adhesive may be placed between the device and the skin, such as for example double-sided medical tape. In one or more embodiments, the device may be secured to the patient using one or more straps, for example straps that are placed around the patient's body or around a body part or parts being treated; straps may be secured for example, without limitation, with Velcro®, buckles, clips, ties, clamps, hooks, magnets, snaps, or any other fastening mechanism. One or more embodiments may use a combination of an adhesive and one or more straps.

In one or more embodiments, the power and wavelength of the radiation emitted by the LEDs may be configured and controlled to optimize penetration to the adipose tissue 103, while also preventing excessive heating of the skin or of tissues other than the adipose tissue. Specific illustrative embodiments for optimal adipose tissue heating are described below.

Figure 2:
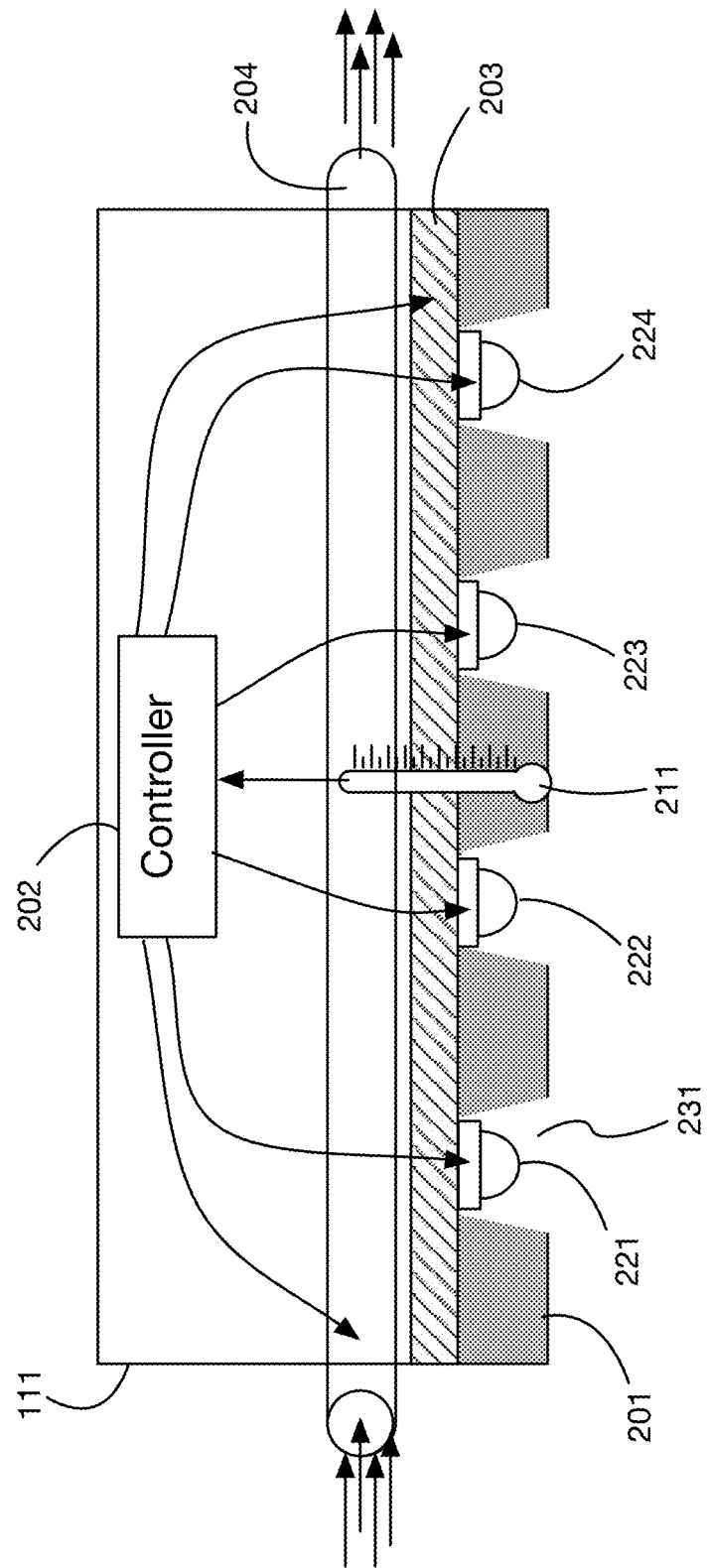
FIG. 2 shows a side view of an embodiment of one section of the invention, illustrating the LEDs, front plate of thermally conductive material, cooling system, and controller that are integrated into the section.

FIG. 2 shows a conceptual cross-sectional view of an illustrative light emitting section such as section 111 from FIG. 1. Front plate 201 is placed on or proximal to the skin of the patient. This plate may comprise for example a heat conducting material that facilitates removal of heat from the skin surface, such as for example, without limitation, copper, aluminum, or another metal. Apertures in the front plate 201 provide paths for the emission of radiation from the LEDs. For example, section 111 has LEDs 221, 222, 223, and 224. Each LED is located within or behind a corresponding aperture in front plate 201. For example, aperture 231 in plate 201 provides an opening for the radiation from LED 221 to reach the patient's tissues. In one or more embodiments, the LEDs may be arranged in a two-dimensional grid or matrix of any desired size, shape, and pattern. LEDs 221 through 224 may provide infrared radiation, as described below; however, in one or more embodiments LEDs may be of any desired wavelength or spectral power distribution. Section 111 may also have one or more temperature sensors. For example, FIG. 2 shows temperature sensor 211. One or more embodiments may include any desired type, modality, arrangement, number, pattern, size, orientation, and shape of temperature sensor or sensors. A temperature sensor may measure the temperature of the patient's skin, the temperature of the LEDs themselves, or any combination thereof. The sensor or sensors may also measure or infer temperature of tissue below the skin. In one or more embodiments, one or more temperature sensors may be infrared temperature sensors. One or more embodiments may use filters in combination with an infrared temperature sensor, where the filters may for example filter out the emitted radiation from the LEDs, and pass only long-wave infrared radiation (emitted for example by the patient's body) to the temperature sensor.

One or more embodiments may include a cooling system to cool either or both of the front plate 201 and the LEDs themselves. The cooling system of the embodiment shown in FIG. 2 includes a thermoelectric (Peltier) cooling element 203, and a water circulation system 204 that may for example remove heat from the hot side of the thermoelectric cooling element. One or more embodiments may use air circulation or heat sinks instead of or in addition to water circulation. One or more embodiments may provide cooling without a thermoelectric cooler, for example using a cooling fluid provided from an external source.

Incorporating a front plate made of a material with high thermal conductivity may facilitate efficient removal of heat from the patient's skin, thereby allowing the system to use more intense radiation without injuring the patient or creating discomfort. A metal front plate in particular may have much higher thermal conductivity than a transparent window such as the windows used in other products. For example, copper has a thermal conductivity of 385 W/m-K, and aluminum has a thermal conductivity of 205 W/m-K; in comparison, transparent materials include glass with a thermal conductivity of 0.8 W/m-K and sapphire with a thermal conductivity of 35 W/m-K. Heat removal from the patient's skin via a front plate with apertures is also more efficient because a cooling element such as Peltier element 203 may be placed behind the front plate along the entire surface of the plate. In contrast, a transparent window is typically cooled only on the edges rather than along its entire surface. The combination of low thermal conductivity of a transparent window and cooling of the window only on the edges dramatically limits the rate of heat removal from a transparent window compared to the front plate with apertures solution illustrated in FIG. 2.

Section 111 also includes a controller 202 that may be coupled for example to any or all of the LEDs, the temperature sensor or sensors, and the components of the cooling system. The controller may be for example a microcontroller or any type of electronics. In one or more embodiments the controller may be remote from the light emitting section 111.

The controller may receive information from the temperature sensor 211, and may modify the power output of the LEDs or the operation of the cooling system in order to maintain the desired temperature of the patient's skin and of the LEDs. In one or more embodiments the controller may be programmed to provide a desired treatment pattern; for example, the controller may energize the LEDs to a desired power for a desired period of time, and then shutdown the LEDs when the treatment is complete.

Figure 3:
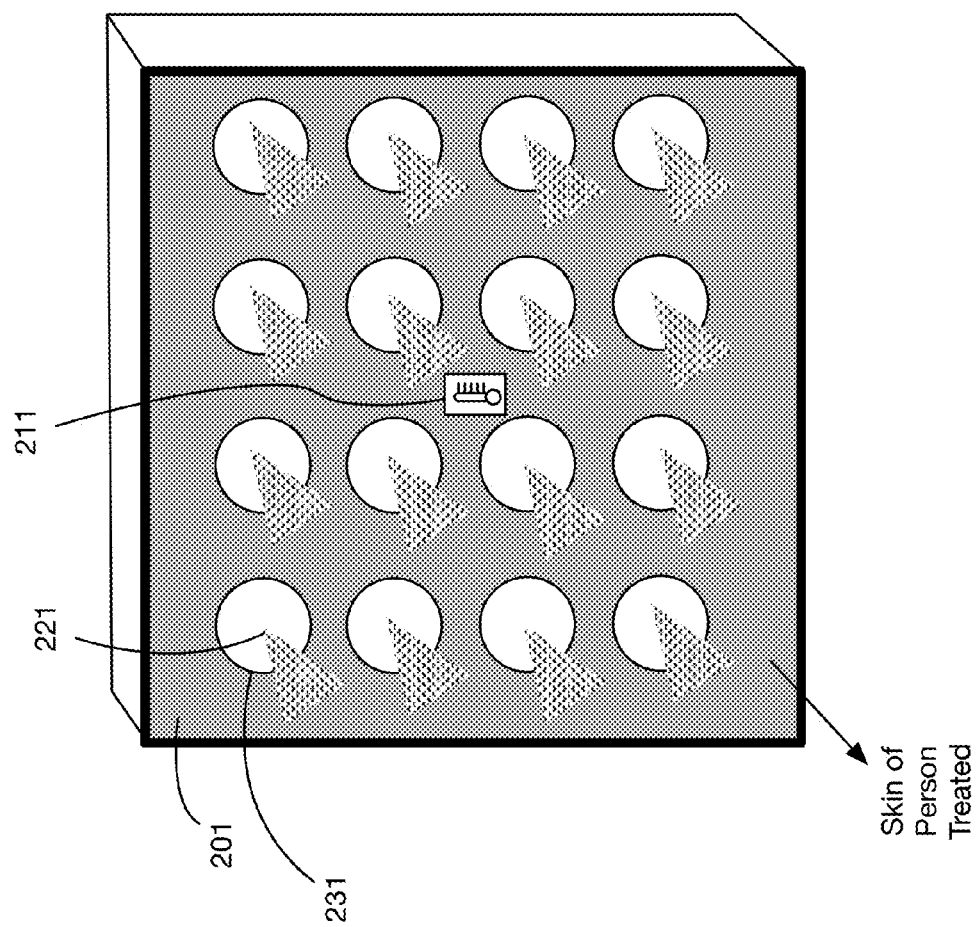
FIG. 3 shows a conceptual diagram of a section of the invention showing the thermally conductive front plate that is placed on or near the patient's skin, which incorporates apertures for a matrix of LEDs.

FIG. 3 shows a view of the embodiment of FIG. 2 looking at the surface that is placed on or proximal to the patient's skin. This view shows an illustrative two-dimensional matrix of LEDs and apertures in the front plate 201. One or more embodiments may arrange LEDs and apertures in any desired pattern. One or more embodiments may place a temperature sensor or sensors in any location with respect to the LEDs and the apertures. In the illustrative example shown in FIG. 3, LEDs such as LED 221 are arranged in a 4×4 matrix, and temperature sensor 211 is in the middle of the matrix. One or more embodiments may use any desired number of temperature sensors and of LEDs. The matrix of LEDs and apertures need not be regular or periodic. Apertures may be of any size and shape, including but not limited to the circular shape illustrated for aperture 231 associated with LED 221. In one or more embodiments, multiple LEDs may be placed behind or within a single aperture. One or more embodiments may have different numbers of LEDs located behind or within different apertures.

Figure 4:
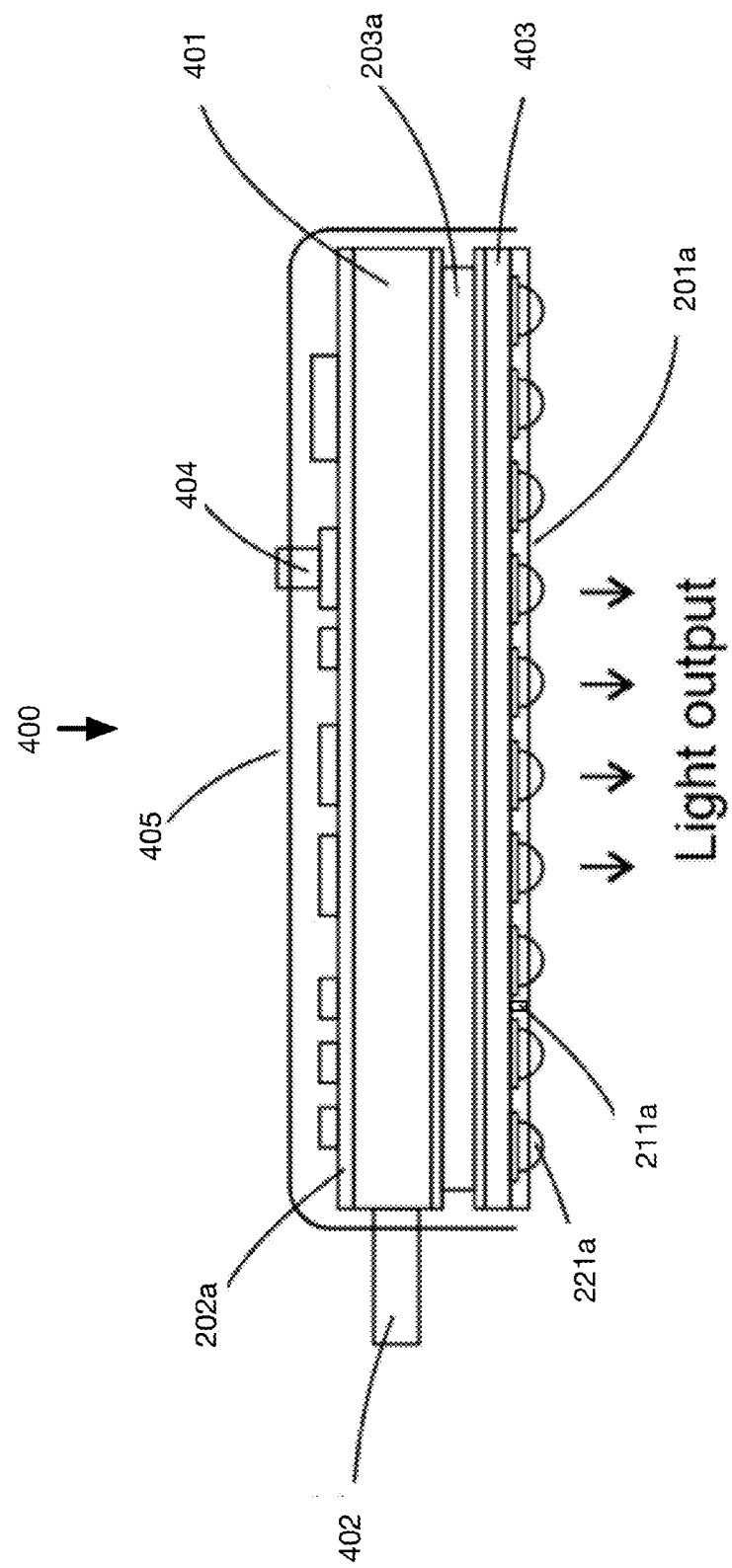
FIG. 4 shows a side view of an embodiment of the invention that is water cooled.

FIGS. 4, 5, and 6A and 6B show other illustrative embodiments of a light emission section. FIG. 4 shows a cross-sectional view of a light emission section 400. The cross section shows an array of 10 LEDs such as LED 221a, with a temperature sensor 211a located between two LEDs. The front plate 201a faces the skin of the patient. This plate may be for example thermally conductive, formed for example from metal, ceramics, or a combination, thereof, and may include sealing such as silicone. One or more temperature sensors such as sensor 211a may be integrated into the front plate 201a. The LEDs such as 221a may be infrared LEDs for example. LEDs may be mounted on board 403, which may be for example a metal core PCB or a ceramic mount. Thermoelectric cooling element 203a is located above the mounting board 403, with the cool side of the element facing the LEDs and the front plate. Water cooler/heat exchanger 401 is located above the hot side of the thermoelectric cooler 203a. Port 402 may provide inflow and outflow of cooling fluid; it may also provide power and communication circuitry. Controller board 202a is located above the heat exchanger 401; the controller may have connections (not shown) to various components such as the LEDs, temperature sensor or sensors, and thermoelectric cooler. On the top of the controller board 202a various indicators and controls may be located, such as a control button or switch 404. Enclosure 405 may surround the components, possibly with openings for controls such as control 404.

FIG. 5 shows a variation 500 of the embodiment of FIG. 4; this device 500 uses air cooling instead of water cooling. LEDs such as 221a, temperature sensors such as 211a, front plate 201a, LED mounting board 403, thermoelectric cooling element 203a, controller board 202a, and control 404 are as described in FIG. 4. Heat sink 503 is located on the hot side of the thermoelectric cooling element 203a, and it is air cooled. Blower or fan 502 may force air over the heat sink. One or more embodiments may not require forced air, and may use passive cooling of the heat sink instead. Port 501 may provide power and communication to the controller board. Enclosure 504 encloses the components.

FIGS. 6A and 6B show top and bottom exploded perspective views of another embodiment of a light emitting section. In this embodiment an internal frame is cooled and this frame draws heat out of a grid on the front of the unit. The LEDs in this embodiment are directly cooled by the water heat exchanger without the thermoelectric cooling element in between. Apertures in the front grid allow light to pass through to the skin, while still providing cooling, and a front glass seals the unit off. Components of this embodiment include, from top to bottom: outer casing 601, which may be for example plastic; controller board 202b; cooling transfer frame 602, which may be for example aluminum or another heat conductive metal or material; thermoelectric cooling element 203b; water heat exchanger lid 603; water heat exchanger body 401b; PCB for mounting LEDs 403b, which may for example have an aluminum core; LED matrix 604; front cooling grid 201b; and front glass 605.

FIG. 7 illustrates the absorption of different wavelengths of radiation by fat tissue (curve 701) and by water (curve 702). (Since water is a major component of other tissues near the skin, water absorption is indicative of the effect of radiation on tissues other than fat). To achieve fat reduction, fat cells should be preferably exposed to a temperature in the mid 40° C. range for a period of time; with this exposure, the loosely connected adipose tissue is damaged and removed over time. Since fat cells do not multiply significantly, much of this tissue is permanently removed. One method of heating sub-surface fat cells is by light irradiation using the selective photothermolysis method—using variations in light absorption of different tissue chromophores. This selective heating is required in order to mostly heat the target tissue to the damage point, not the surrounding tissue. The subdermal circulation with active liquid (blood) transport helps to cool these tissues, whereas the adipose tissue will store heat energy for longer.

To effectively and selectively heat sub-surface structures three conditions must be met: (1) The tissue to be treated must have a chromophore that absorbs the radiant energy well, preferably more than the surrounding tissues. (2) The absolute absorption of the tissues must be at such a level, that the radiant energy is not delivered primarily to the dermal structures the energy passes through. (3) The remaining energy at the target tissue after passing through other tissue structures must be enough to heat the tissue to the desired level (in this case where cell damage occurs).

Even though some radiant light wavelengths are highly absorbed by adipose tissue, such as around 1200 nm and 1700 nm, these absorption peaks have much higher absorption in water (×10 and ×50 compared to 930 nm) and other chromophores and reaching the target tissue with sufficient energy without damaging overlaying structures would be nearly impossible. An optimal tradeoff between heating fat tissue and avoiding overheating of other tissues is therefore approximately at the peak value 703 for fat absorption, which is at a wavelength of approximately 930 nm. At this peak the absorption rises to a maximum of 0.13 cm$^{-1}$. This means that about a third of the light is left at 7-8 cm when sent through a fat layer. In water the absorption at this wavelength is about the same at 0.12 cm$^{-1}$. Thus FIG. 7 shows that at 930 nm the mammalian fat is absorbing roughly the same amount of energy as the water.

Even though the absorption difference between the target tissue and the surrounding tissues is not great at approximately 930 nm, the situation can be improved by the easy access to upper tissue structures. The upper tissues can be cooled from the skin surface, protecting them from heat damage. The temperature of the adipose tissue versus overlaying tissues is a function of the applied cooling, active dermal transport and the relative absorption of the various skin layer chromophores. This temperature profile can be monitored with embedded sensors or via simple patient feedback.

LEDs in the 9XXnm wavelength range with power output of watts are available and are efficient (35-40%). The security illumination market among others have driven development of LED devices in this wavelength range, where low cost silicon camera sensors are sensitive. FIG. 8 shows the typical spectral output of an efficient 940 nm LED emitter. The peak 801 corresponds roughly to the desired peak 703 in FIG. 7 for maximum absorption of radiation by fat cells. In one or more embodiments filters may be applied to the LED output to concentrate the delivered radiation in the desired range. For example, a bandpass filter may be applied to limit the output of the LEDs to the range 802, which is approximately 920 to 950 mm, in order to maximize the effect on fat cells while also minimizing the effect on surrounding tissues. One or more embodiments may use any type of filter, including for example, without limitation, a high pass filter, a low pass filter, and a band pass filter. The output range 802 is illustrative; one or more embodiments may modify the delivered spectral power in any desired manner using any type or types of filters. Filters could be integrated for example into a lens or into a glass covering such as glass 605 of FIG. 6A.

Figure 9:
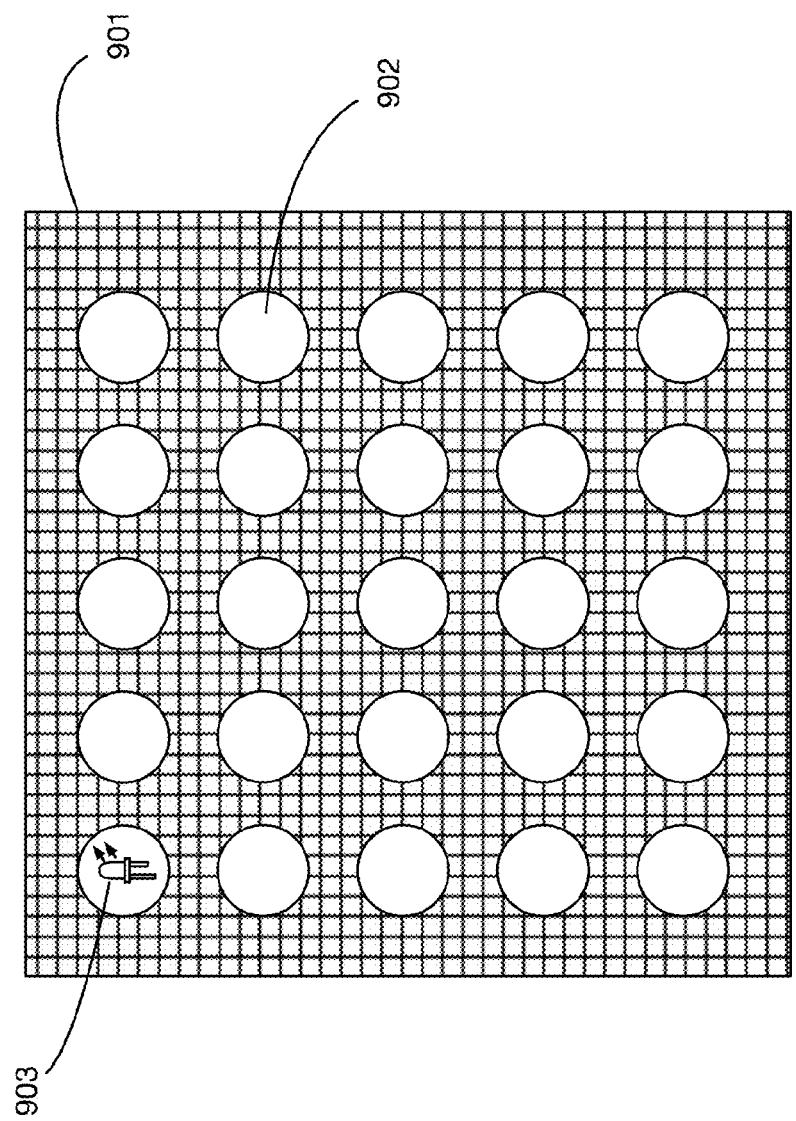
FIG. 9 shows a conceptual diagram of the front plate (facing the skin) of an embodiment of the invention, with a cooling surface that has apertures through which LED light is emitted.
Figure 10:
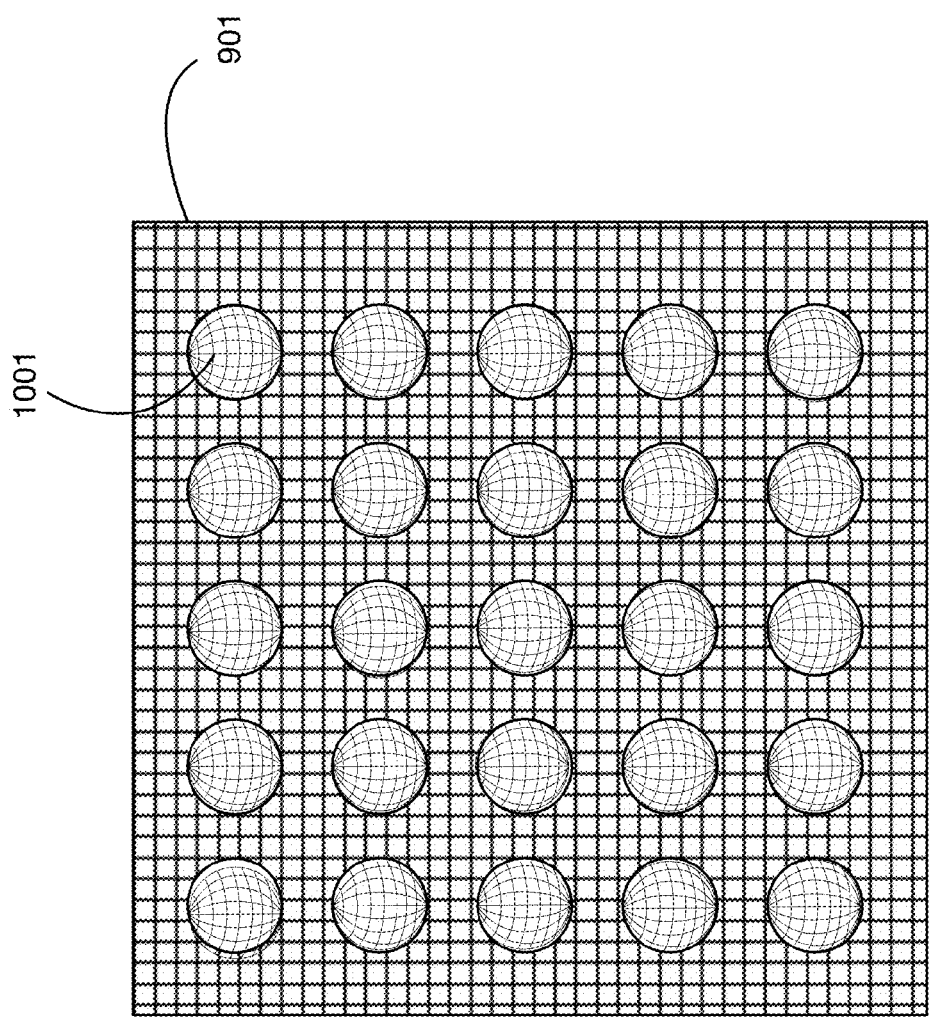
FIG. 10 shows a variation of the embodiment of FIG. 9, which has protruding transparent covers over the LEDs.
Figure 11:
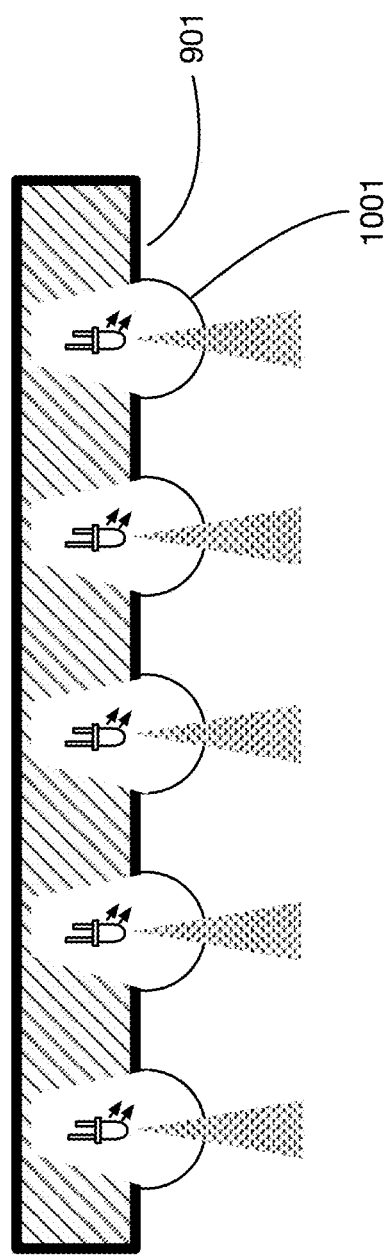
FIG. 11 shows a side view of the embodiment of FIG. 10.
Figure 12:
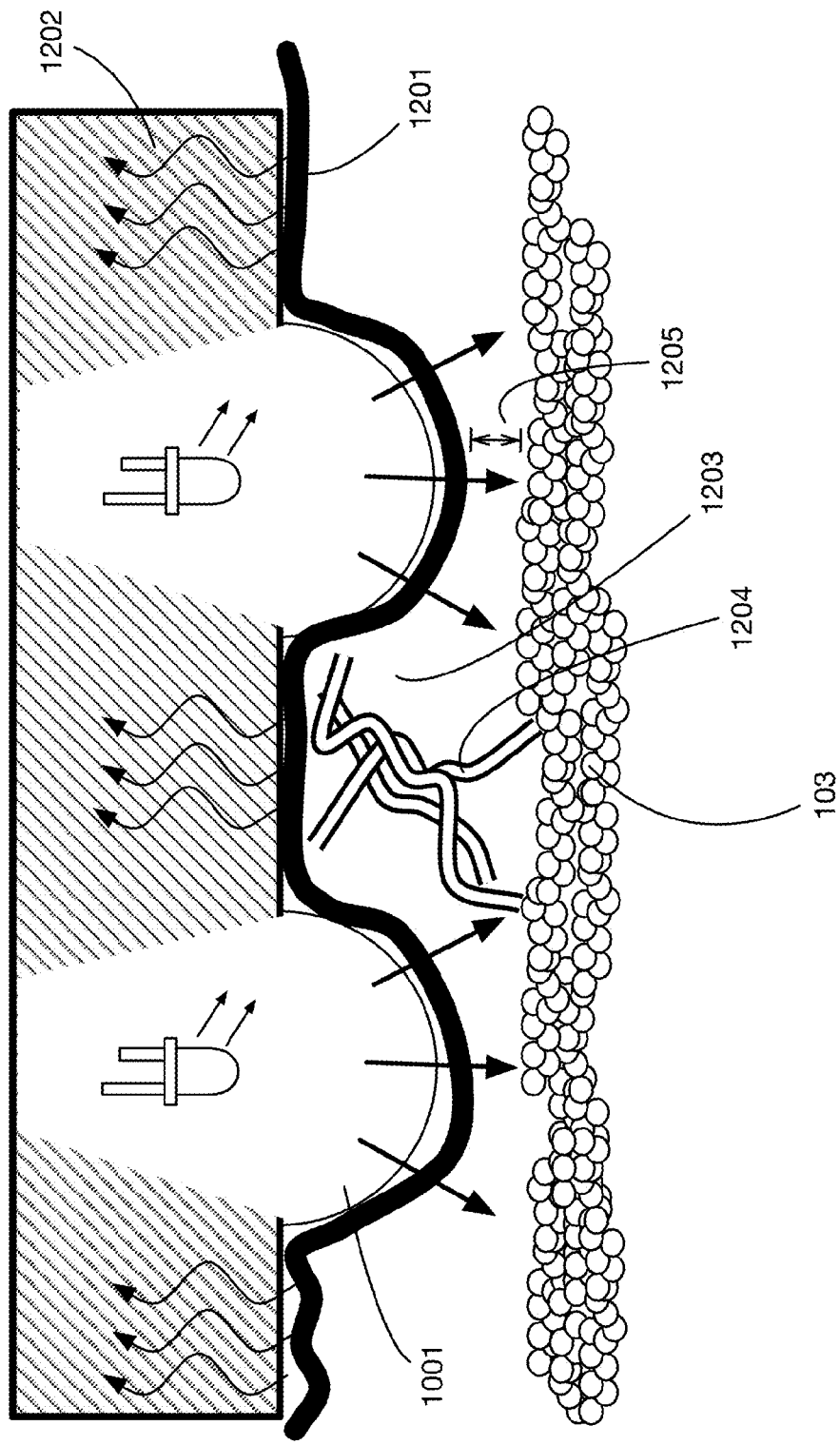
FIG. 12 shows a close-up view of the embodiment of FIGS. 10 and 11 applied to the patent's skin, illustrating how the protrusions provide the LED radiation more directly to the adipose layer, while allowing blood flow and heat removal from the areas between the protrusions.

In one or more embodiments, the surface facing the patient serves two purposes: it provides paths for radiation from the LEDs to reach the skin and penetrate the subcutaneous tissue, and it cools the skin surface to remove heat from tissue other than the adipose tissue. FIG. 9 illustrates an embodiment with a front plate 901, which may for example be made of a heat conducting material such as aluminum or copper (or any other thermally conductive material or materials) in order to remove heat from the skin surface. Apertures such as aperture 902 in the plate 901 provide a path for emission of light from LEDs such as LED 903 that are located behind the plate. Apertures may be covered for example with a transparent material such as glass or plastic to allow radiation to reach the skin and the underlying tissues. In one or more embodiments these transparent materials may be lenses. In one or more embodiments the front plate may have protrusions where the LEDs are located, in order to bring the radiation closer to the adipose tissue. FIG. 10 shows an illustrative embodiment in which the areas such as 1001 enclosing the LEDs protrude outward (towards the skin) from the surface of the front plate 901. FIG. 11 shows a cross-sectional view of the embodiment shown in FIG. 10. A benefit of embodiments with protrusions for the LED is that the protrusions compress the tissue under the skin, thereby reducing the distance that radiation travels to reach the adipose tissue. By reducing this distance, absorption of the radiation by the tissue above the adipose tissue is minimized. This effect is illustrated in FIG. 12, which shows a close-up view of the embodiment of FIG. 11 placed against the skin of a patient. Indentations are formed in the skin 1201 of the patient by the protrusions such as 1001 that surround the LEDs. These indentations reduce the distance 1205 between the LEDs and the adipose tissue 103. In the areas between the protrusions, the tissue under the skin is not compressed. These regions, such as region 1203, therefore provide blood flow via blood vessels such as 1204 in order to remove heat from the tissues above the adipose layer 103. The contact of the skin in these regions between the LED protrusions with the heat conductive surface of the front plate also provides heat removal 1202 to pull heat away from these tissues. Therefore, the combination of the LED protrusions and the heat conducting front plate maximize the relative radiation absorbed by adipose tissue versus the radiation absorbed by other tissues, thereby maximizing the effectiveness of the device to remove fat.

Figure 13:
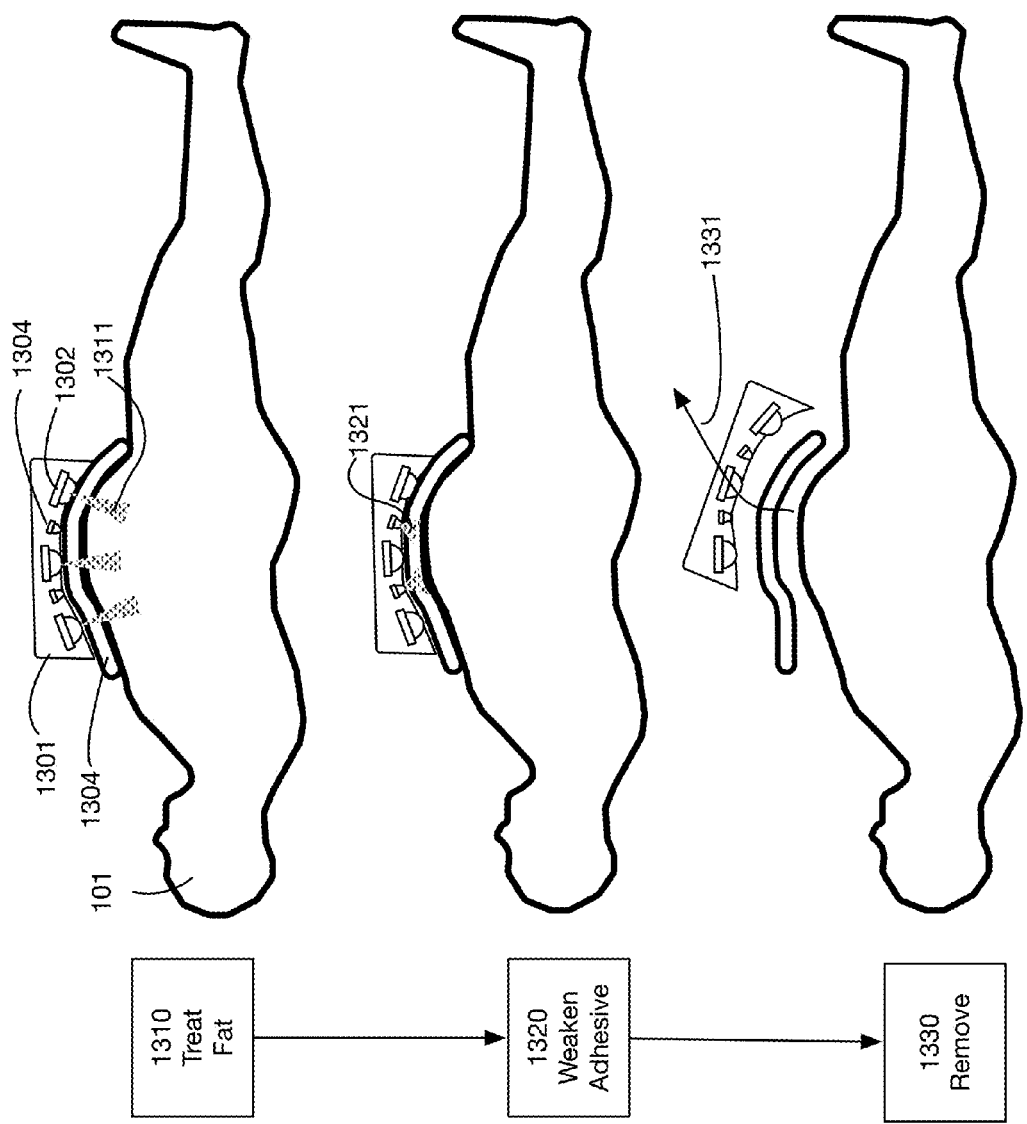
FIG. 13 shows an embodiment of the invention that includes ultraviolet LEDs (in addition to the infrared LEDs for fat treatment); these ultraviolet LEDs may be used to weaken an adhesive that is used to attach the device to the patient during treatment.

In one or more embodiments, the light emitting section or sections may be attached to the patient's skin using an adhesive, such as for example a double-sided single-use medical grade adhesive. One or more embodiments may incorporate components that may assist in detaching the device, for example by weakening the adhesive that attaches the device to the skin. For example, an adhesive release may be achieved by illuminating the adhesive with a low amount of ultraviolet light, which reduces the adhesion strength of the adhesive to the point of a skin friendly mechanical release of the light emitting section from the tissue. Therefore, one or more embodiments may include one or more ultraviolet (UV) LEDs embedded into the light emitting section, which may be activated upon completion of the treatment. FIG. 13 illustrates an embodiment that incorporates such a UV light release mechanism. Light emitting section 1301 includes both infrared LEDs such as LED 1302 and (potentially lower powered) ultraviolet LEDs such as LED 1304. The light emitting section 1301 is attached to patient 101 via adhesive 1304 to initiate treatment. During the treatment phase 1310, infrared radiation 1311 is emitted from the infrared LEDs. After completion of treatment, the controller (or the patient or an operator) initiates the weaken adhesive phase 1320. In this phase the infrared LEDs are switched off, and the ultraviolet LEDs are energized to direct ultraviolet radiation 1321 at the adhesive to weaken the adhesive. The patient or an operator can then perform removal 1330 of the device and the adhesive manually by pulling 1331.

Instead of or in addition to an adhesive, one or more straps may be used to secure the device to the patient during treatment. Straps may be placed around the patient's body or around a body part or parts being treated; straps may be secured for example, without limitation, with Velcro®, buckles, clips, ties, clamps, hooks, magnets, snaps, or any other fastening mechanism. One or more embodiments may use a combination of an adhesive and one or more straps.

Figure 14:
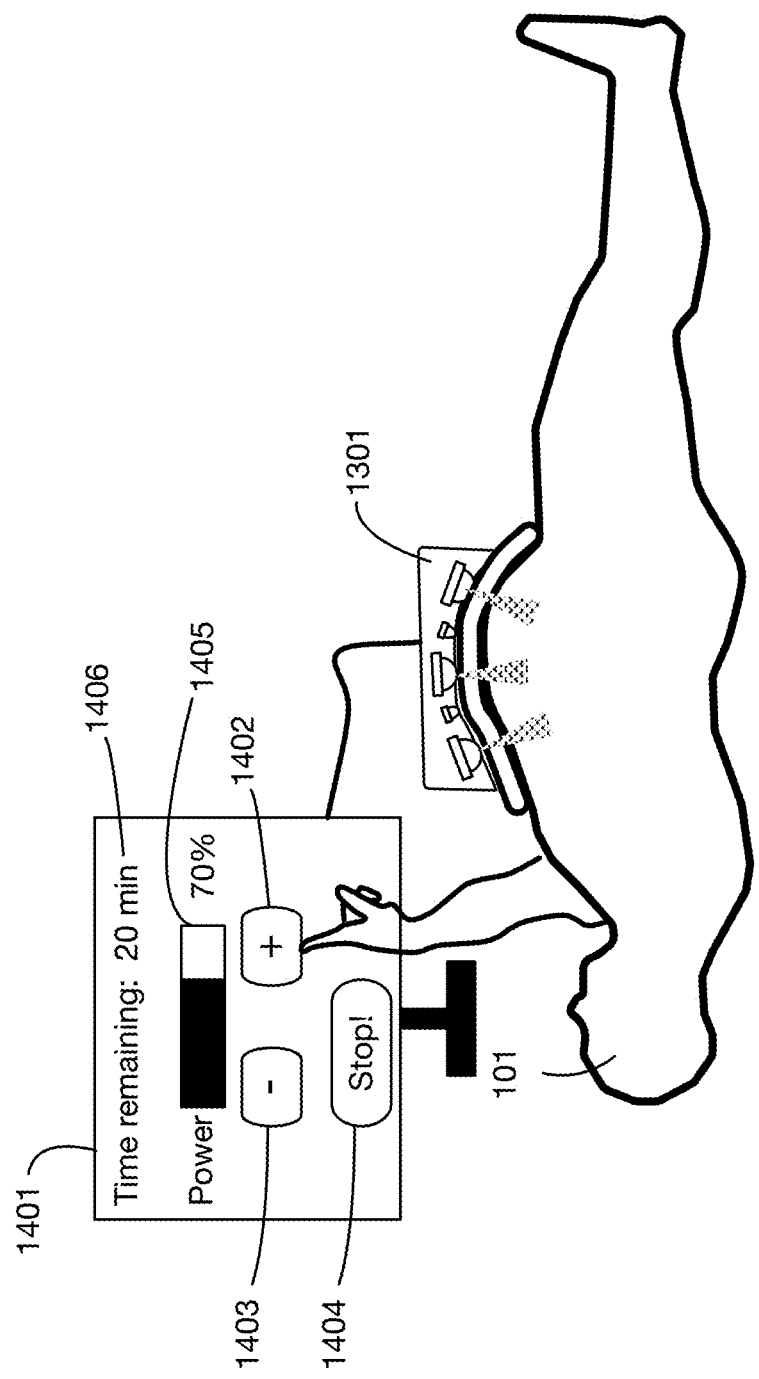
FIG. 14 shows an embodiment of the invention that includes a user control device that may be used by the patient or by treatment personnel to monitor and adjust the treatment intensity.

One or more embodiments may include one or more user control or user interface devices or applications that may control various aspects of the treatment, and may report information on treatment conditions and treatment progress. FIG. 14 illustrates an embodiment with a control station 1401 coupled to a light emitting section 1301. Control stations may be coupled to one or more light emitting sections via wired or wireless connections. For ease of illustration this control station is shown as a large touch-screen device; this embodiment is illustrative, and one or more embodiments may use any type of device or application as a control station. Control stations may be used for example by patients themselves, by treatment personnel, or by any combination thereof. Illustrative controls may include for example, without limitation, a control 1402 to increase the intensity of the radiation, a control 1403 to decrease the intensity of the radiation, and a control 1404 to stop radiation completely. The control station may also display information such as the time remaining 1406 for the treatment, and the current power level 1405. One or more embodiments may display temperature information and may provide options to set the desired temperature or to set a desired temperature range for the treatment. One or more embodiments may display a map of the temperature measurements across the treatment area. In embodiments that include ultraviolet LEDs for adhesive release, one or more embodiments may include controls to initiate the adhesive release phase, or controls to modify the intensity of the ultraviolet radiation directed at the adhesive. One or more embodiments may display information estimating the amount of fat destroyed during the treatment session, or during a series of treatment sessions.

While the invention herein disclosed has been described by means of specific embodiments and applications thereof, numerous modifications and variations could be made thereto by those skilled in the art without departing from the scope of the invention set forth in the claims.

What is claimed is:

1. An LED matrix system for subcutaneous fat reduction with an efficient cooling surface comprising:
   one or more light emission sections, each section of said one or more light emission sections comprising
      a front plate configured to be placed on or proximal to the skin of a person, said front plate comprising a thermally conductive material, said front plate having a plurality of apertures;
      a plurality of LEDs corresponding to said plurality of apertures, and disposed to irradiate said skin of said person, wherein each LED of said plurality of LEDs is located in or behind a corresponding aperture of said plurality of apertures to allow light to reach said skin of said person,
         wherein said plurality of LEDs are offset behind a treatment surface of said skin of said person in a direction away from said skin of said person to distribute radiation from said plurality of LEDs evenly across said treatment surface;
      at least one temperature sensor disposed to measure a temperature of said skin of said person;
      a cooling system that cools
         said front plate,
         said skin of said person, and
         said plurality of LEDs;
      a transparent covering over each aperture of said plurality of apertures,
         wherein each of said transparent covering over each aperture of said plurality of apertures protrudes from said front plate toward said skin of said person as a transparent protrusion, and
         wherein each transparent protrusion over each aperture compresses said skin of said person under said transparent protrusion configured to bring said plurality of LEDs closer to adipose tissue of said skin of said person
            to reduce a distance between said plurality of LEDs and said skin of said person,
            to allow light from said plurality of LEDs to pass through to reach said skin of said person, and
            to allow reduction of absorption of said radiation by tissue other than said adipose tissue of said skin of said person above said adipose tissue,
         wherein said cooling system cools said skin of said person to remove heat from said tissue other than said adipose tissue,
         wherein indentations are formed in said skin of said person by said transparent protrusions that reduce said distance between said plurality of LEDs and said adipose tissue, and
         wherein in areas between said transparent protrusions, said skin of said person is not compressed; and,
   a controller coupled to one or more of said plurality of LEDs, said at least one temperature sensor, and said cooling system, wherein said controller is configured to maintain said temperature of said skin of said person within a target range.

2. The LED matrix system of claim 1 wherein
   said one or more light emission sections comprise a plurality of light emissions sections;
   said plurality of light emission sections are coupled via non-rigid couplings that allow each section to pivot with respect to one or more other sections.

3. The LED matrix system of claim 1 wherein
   said plurality of LEDs each have a spectral power distribution with a peak in the range of 920 nanometers to 950 nanometers.

4. The LED matrix system of claim 3 wherein said controller is further configured to maintain a temperature of said plurality of LEDs in an LED target operating temperature range to maintain said peak in said range of 920 nanometers to 950 nanometers.

5. The LED matrix system of claim 1 wherein
   said plurality of LEDs irradiate said skin with at least 1 watt per centimeter squared.

6. The LED matrix system of claim 1 wherein
   said thermally conductive material comprises a metal.

7. The LED matrix system of claim 6 wherein
   said metal comprises copper.

8. The LED matrix system of claim 6 wherein
   said metal comprises aluminum.

9. The LED matrix system of claim 1 wherein said transparent covering comprises a lens.

10. The LED matrix system of claim 1 wherein said cooling system comprises a thermoelectric cooling element.

11. The LED matrix system of claim 10 wherein said cooling system further comprises a water circulation system.

12. The LED matrix system of claim 11 wherein said water circulation system comprises a connection to a water source that is external to said one or more light emission sections.

13. The LED matrix system of claim 10 wherein said cooling system further comprises an air circulation system.

14. The LED matrix system of claim 1 further comprising a user interface coupled to said controller associated with each section of said one or more light emission sections, wherein said user interface comprises controls to
   increase energy delivered by said one or more light emission sections;
   decrease energy delivered by said one or more light emissions sections; and,
   shutdown energy delivery by said one or more light emission sections.

15. The LED matrix system of claim 1 further comprising one or more wavelength filters between said plurality of LEDs and said skin of said person.

16. The LED matrix system of claim 1 wherein said one or more wavelength filters comprise a bandpass filter with a pass band within a range of 920 nanometers and 950 nanometers.

17. The LED matrix system of claim 1 wherein said front plate of at least one of said one or more light emission sections is curved to conform to a body part of said person.

18. The LED matrix system of claim 1 wherein
   each said section further comprises a plurality of ultraviolet LEDs that provide radiation to weaken an adhesion strength of an adhesive placed between said front plate and said skin of said person;

each controller is further configured to activate said plurality of ultraviolet LEDs at the end of a treatment session to facilitate removal of said section from said adhesive.

19. A temperature controlled LED matrix for subcutaneous fat reduction comprising:
a plurality of light emission sections, each section of said plurality of light emission sections comprising
a front plate configured to be placed on or proximal to the skin of a person, said front plate comprising a thermally conductive material, said front plate having a plurality of apertures;
a plurality of LEDs corresponding to said plurality of apertures, and disposed to irradiate said skin of said person, wherein
each LED of said plurality of LEDs is located in or behind a corresponding aperture of said plurality of apertures to allow light to reach said skin of said person;
each LED of said plurality of LEDs has a spectral power distribution with a peak in the range of 920 nanometers to 950 nanometers;
said plurality of LEDs irradiate said skin below said front plate with at least 1 watt per centimeter squared;
said plurality of LEDs are offset behind a treatment surface of said skin of said person in a direction away from said skin of said person to distribute radiation from said plurality of LEDs evenly across said treatment surface;
at least one temperature sensor disposed to measure a temperature of said skin of said person;
a cooling system comprising
a thermoelectric cooling element;
one or both of a water circulation system and an air circulation system;
wherein said cooling system is configured to cool
said front plate,
said skin of said person, and
said plurality of LEDs;
a transparent covering over each aperture of said plurality of apertures,
wherein each of said transparent covering over each aperture of said plurality of apertures protrudes from said front plate toward said skin of said person as a transparent protrusion,
wherein each of said transparent covering over each aperture of said plurality of apertures protrudes from said front plate toward said skin of said person as a transparent protrusion, and
wherein each transparent protrusion over each aperture compresses said skin of said person under said transparent protrusion configured to bring said plurality of LEDs closer to adipose tissue of said skin of said person
to reduce a distance between said plurality of LEDs and said skin of said person,
to allow light from said plurality of LEDs to pass through to reach said skin of said person, and
to allow reduction of absorption of said radiation by tissue other than said adipose tissue of said skin of said person above said adipose tissue,
wherein said cooling system cools said skin of said person to remove heat from said tissue other than said adipose tissue,
wherein indentations are formed in said skin of said person by said transparent protrusions that reduce said distance between said plurality of LEDs and said adipose tissue, and
wherein in areas between said transparent protrusions, said skin of said person is not compressed; and
a controller coupled to one or more of said plurality of LEDs, said at least one temperature sensor, and said cooling system, wherein said controller is configured to
maintain said temperature of said skin of said person within a target range; and
maintain a temperature of said plurality of LEDs in an LED target operating temperature range to maintain said peak in said range of 920 nanometers to 950 nanometers;
a user interface coupled to said controller associated with each section of said plurality of light emission sections, wherein said user interface comprises controls to
increase energy delivered by said plurality of light emission sections;
decrease energy delivered by said plurality of light emissions sections; and,
shutdown energy delivery by said plurality of light emission sections;
wherein said plurality of light emission sections are coupled via non-rigid couplings that allow each section to pivot with respect to one or more other sections.

* * * * *